(12) United States Patent
Ting et al.

(10) Patent No.: US 7,883,666 B2
(45) Date of Patent: Feb. 8, 2011

(54) DISSECTION APPARATUS WITH TOOL EXCHANGING MECHANISM

(75) Inventors: Chun-Chien Ting, Yunlin (TW); Jan-Hao Chen, Changhua (TW); Yeou-Bin Guu, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 956 days.

(21) Appl. No.: 11/741,716

(22) Filed: Apr. 27, 2007

(65) Prior Publication Data

US 2008/0161842 A1     Jul. 3, 2008

(30) Foreign Application Priority Data

Dec. 29, 2006   (TW)   ............................... 95149895 A (51) Int. Cl.
*G01N 21/00* (2006.01)
(52) U.S. Cl. .............................. 422/63; 422/64; 422/65; 422/99; 422/100; 83/411.1; 83/915.5; 83/468.7
(58) Field of Classification Search ............. 422/63–65, 422/99–100; 83/411.1, 915.5, 468.7
See application file for complete search history.

(56) References Cited

U.S. PATENT DOCUMENTS 6,673,086 B1    1/2004   Hofmeier et al.

FOREIGN PATENT DOCUMENTS

TW         I236500          7/2005

*Primary Examiner*—Jyoti Nagpaul (57) ABSTRACT

A dissection apparatus is disclosed. The dissection apparatus includes a supporting mechanism, a holder, a driving element rotating the holder, a cam fixed to the supporting mechanism, a first sliding element, a second sliding element, a dissecting device disposed on the first sliding element, an aspirating device disposed on the second sliding element. When the holder rotates to move the dissecting device from a first idle position to an operating position, the first sliding element is lowered by the guide of the cam enabling the aspirating device to move from the operating position to a second idle position. When the holder rotates to move the aspirating device from the second idle position to the operating position, the guide of the cam lowers the second sliding element, thus, allowing the dissecting device is able to move from the operating position to the first idle position.

15 Claims, 12 Drawing Sheets

DISSECTION APPARATUS WITH TOOL EXCHANGING MECHANISM

BACKGROUND OF THE INVENTION

1. Field of the Invention

The invention relates to a dissecting apparatus, and more particularly to a dissecting apparatus with a tool exchanging mechanism.

2. Description of the Related Art

With advances in biotechnology, the number of labor intensive operations on organisms, such as dissection and aspiration, has increased. The cultivation of human embryonic stem cells is provided as an example. Embryonic stem cells are cultivated in a container as a group. As the cell group grows, the embryonic stem cells can easily be converted into cells having different qualities. When harvesting a group of cells, the operator must dissect the cell group into smaller groups for removal to other containers for further cultivation. Although cell cultivation has not been fully automated, semi-automatic apparatuses are often used, such as the dissecting device disclosed in U.S. Pat. No. 6,673,086.

BRIEF SUMMARY OF INVENTION

Dissection apparatuses are provided. An exemplary embodiment of a dissection apparatus of the invention comprises: a supporting mechanism; a holder rotatably disposed on the supporting mechanism; a driving element disposed on the supporting mechanism to rotate the holder; a cam fixed to the supporting mechanism; the holder rotating relative to the cam; a first sliding element slidably disposed on the holder and lifted or lowered thereon by the guide of the cam; a second sliding element slidably disposed on the holder and lifted or lowered thereon by the guide of the cam; a dissecting device disposed on the first sliding element and an aspirating device disposed on the second sliding element. When the holder rotates to move the dissecting device from a first idle position to an operating position, the first sliding element is lowered by the guide of the cam, and the aspirating device is moved from the operating position to a second idle position with the second sliding element lifted by the guide of the cam. When the holder rotates to move the aspirating device from the second idle position to the operating position, the second sliding element is lowered by the guide of the cam, and the dissecting device is moved from the operating position to the first idle position with the first sliding element lifted by the guide of the cam.

The cam comprises a track having a lowest point corresponding to the operating position and two highest points corresponding to the first idle position and the second idle position. The first sliding element has a first guiding element abutting the track. The first sliding element, guided by the cam, slides on the holder. The second sliding element has a second guiding element abutting the track. The second sliding element, guided by the cam, slides on the holder.

The holder comprises a shaft with first and second arms extending from the shaft. The first sliding element is slidably disposed on the first arm and the second sliding element is slidably disposed on the second arm.

The cam further comprises a cylindrical body and a track disposed on the periphery of the cylindrical body to guide the first sliding element and the second sliding element. The cylindrical body has a hole through which the shaft extends, allowing the holder to rotate relative to the cam.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION OF INVENTION

Figure 1:
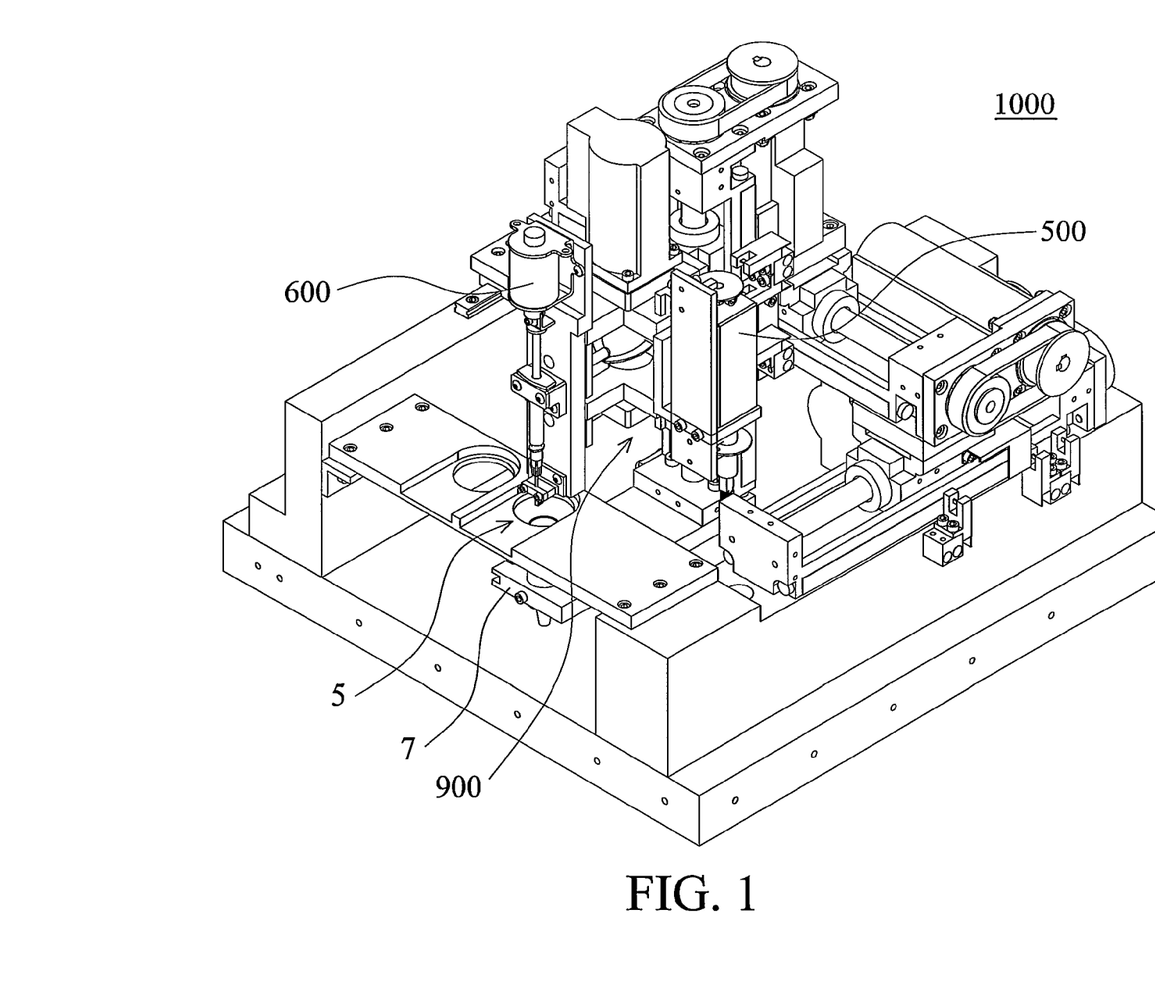
FIG. 1 is a perspective view of a dissection apparatus of the invention.

Referring to FIG. 1, a dissection apparatus 1000 of the invention comprises a tool exchanging mechanism 900 capable of rapidly exchanging and positioning a dissecting device 500 and an aspirating device 600. The dissection apparatus 1000 has an operating area 5 where the dissecting device 500 or the aspirating device 600 performs dissection or aspiration operations. A monitoring device 7 is disposed under the operating area 5 to monitor the operation. The idle device is moved to its own idle position. The structure of the tool exchanging mechanism 900 is described in the following.

Figure 2:
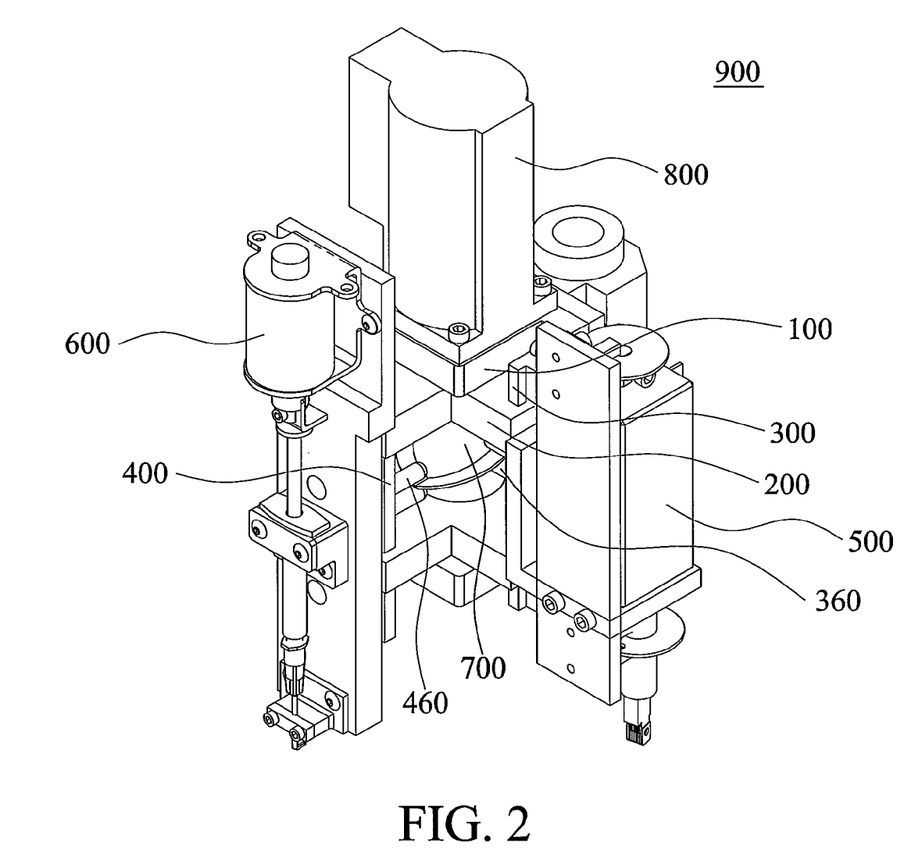
FIG. 2 is a perspective view of an embodiment of a tool exchanging mechanism of the invention.

Referring to FIG. 2, the dissecting device 500 and the aspirating device 600 are disposed on two sides of the tool exchanging mechanism 900. The tool exchanging mechanism 900 comprises a supporting mechanism 100, a holder 200, a first sliding element 300, a second sliding element 400, a cam 700 and a motor (driving element) 800.

Figure 3:
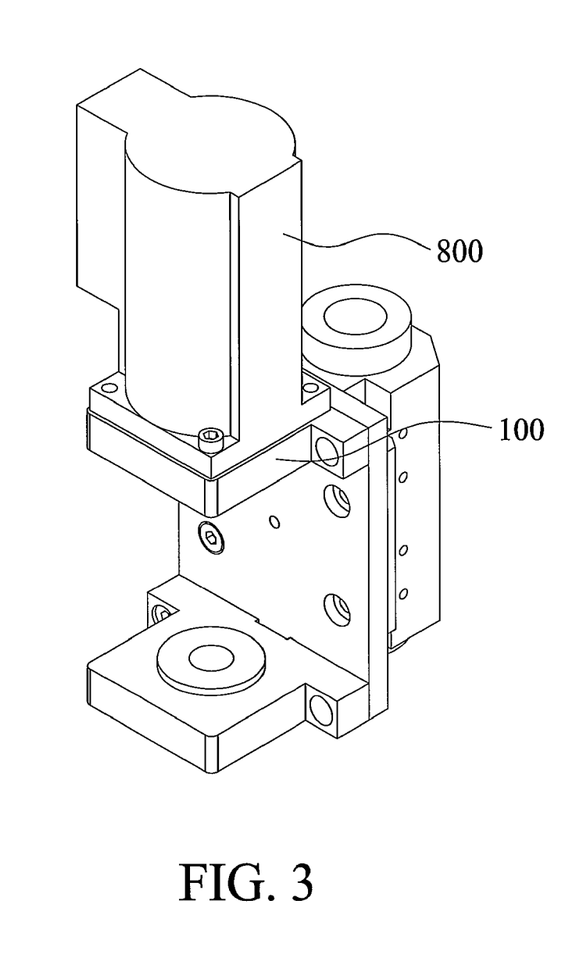
FIG. 3 is a schematic view depicting a motor disposed on a supporting mechanism.
Figure 4:
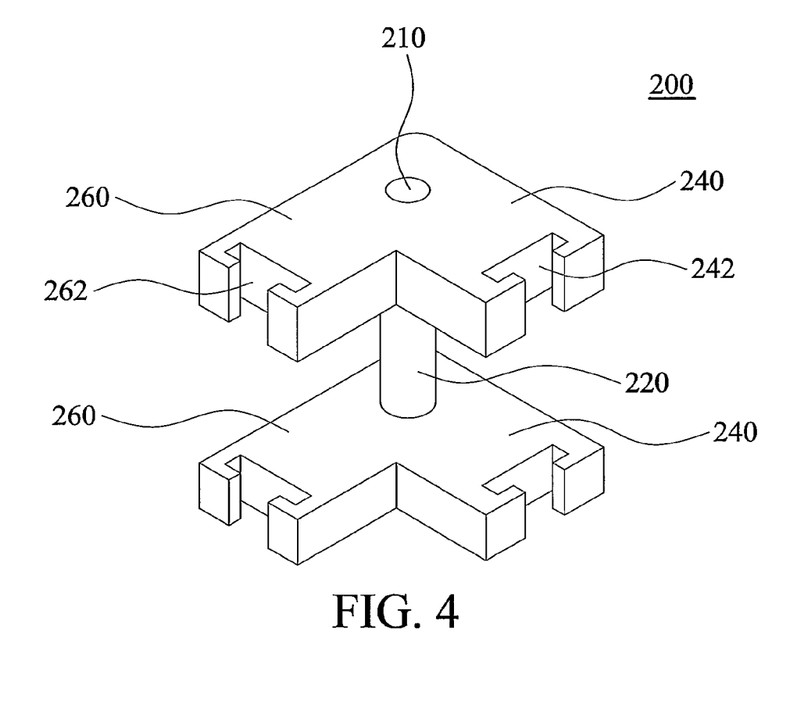
FIG. 4 is a perspective view of an embodiment of a holder of the invention.

Referring to FIGS. 3 and 4, the holder 200 comprises a shaft 220, two first arms 240 and two second arms 260. The first arms 240 and the second arms 260 extend from the shaft 220. A first channel 242 is formed on the first arm 240, and a second channel 262 is formed on the second arm 260. The axis of the motor 800 engages a hole 210 axially formed on the shaft 220 to rotate the holder 200. In this embodiment, the first arm 240 and the second arm 260 are perpendicular.

Figure 5:
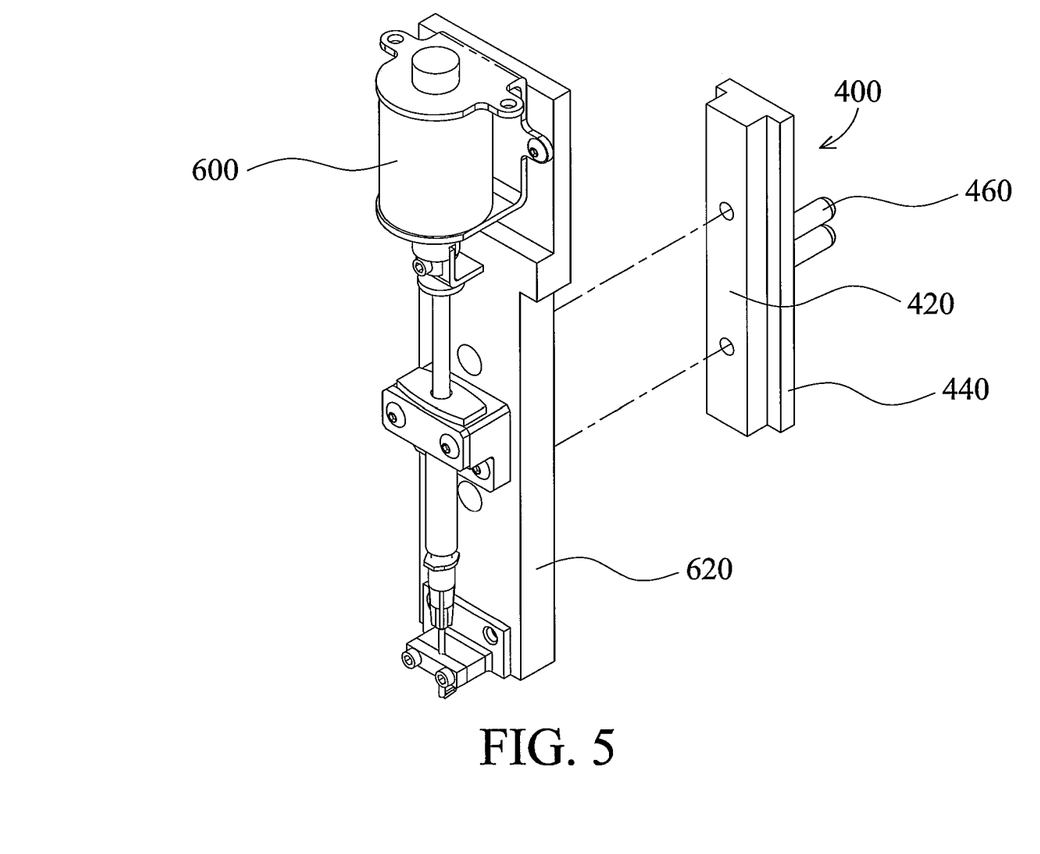
FIG. 5 is an exploded view of a second sliding element and an aspirating device of the invention.

FIG. 5 depicts the second sliding element 400 and the aspirating device 600. Because the structures of the first sliding element 300, and the second sliding element 400, are identical, only the second sliding element 400 is described. The second sliding element 400 comprises a connecting portion 420, two second flanges 440 (the first sliding element has two first flanges) and a second guiding element 460. The connecting portion 420 is connected to a connecting element 620 to which the aspirating device 600 is fixed. The second flange 440 extends from the lateral sides of the connecting portion 420 and is slidably joined to the second channel 262.

Figure 6:
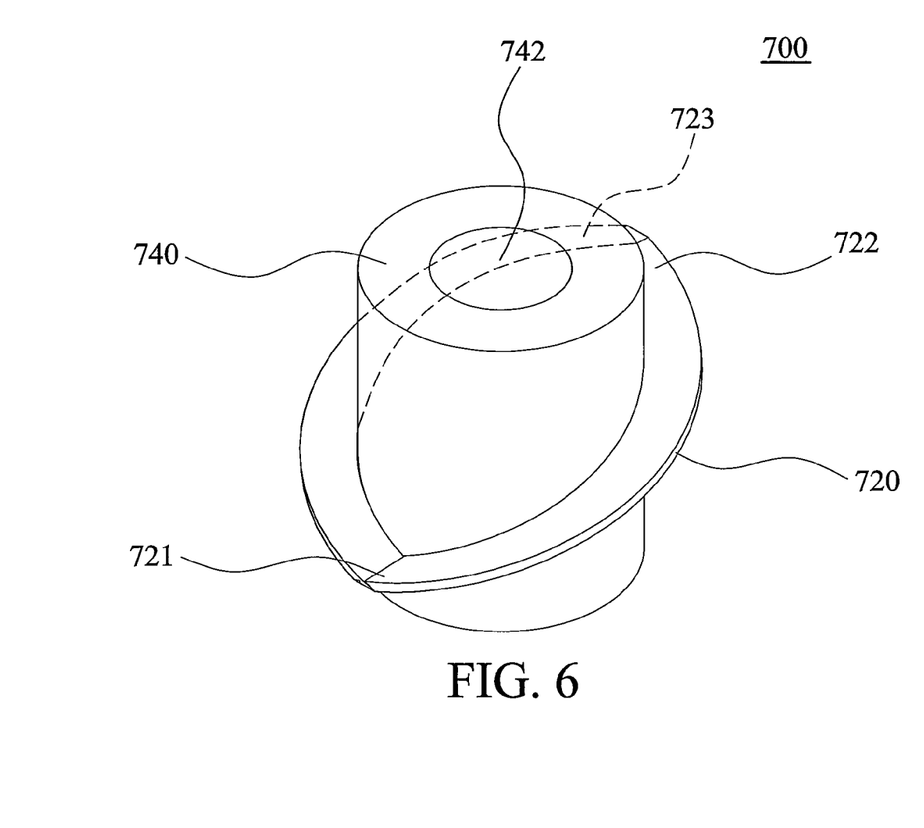
FIG. 6 is a perspective view of an embodiment of a cam of the invention.

The second guiding element 460 is fork-shaped and abuts the track 720 of the cam 700. FIG. 6 is a perspective view of the cam 700. The cam 700 comprises a main body 740 and a track 720. The main body 740 is cylindrical and has a hole 742. The track 720 protrudes from the periphery of the main body 740 and has a lowest point 721 corresponding to the operating position and two highest points 722 and 723 corresponding to a first idle position for the dissecting device 500 and a second idle position for the aspirating device 600. The shaft 220 extends through the hole 742, and the cam 700 is fixed to the supporting mechanism 100 by a positioning pin (not shown), thus, the holder 200 is rotatable relative to the cam 700.

Referring again to FIG. 2, the fork-shaped second guiding element 460 holds the track 720. Similarly, the first guiding element 360 holds the track 720. In FIG. 2, as the second guiding element 460 is at the lowest point 721, the aspirating device 600 is in the operating position and the dissecting device 500 is in the first idle position.

Figure 7:
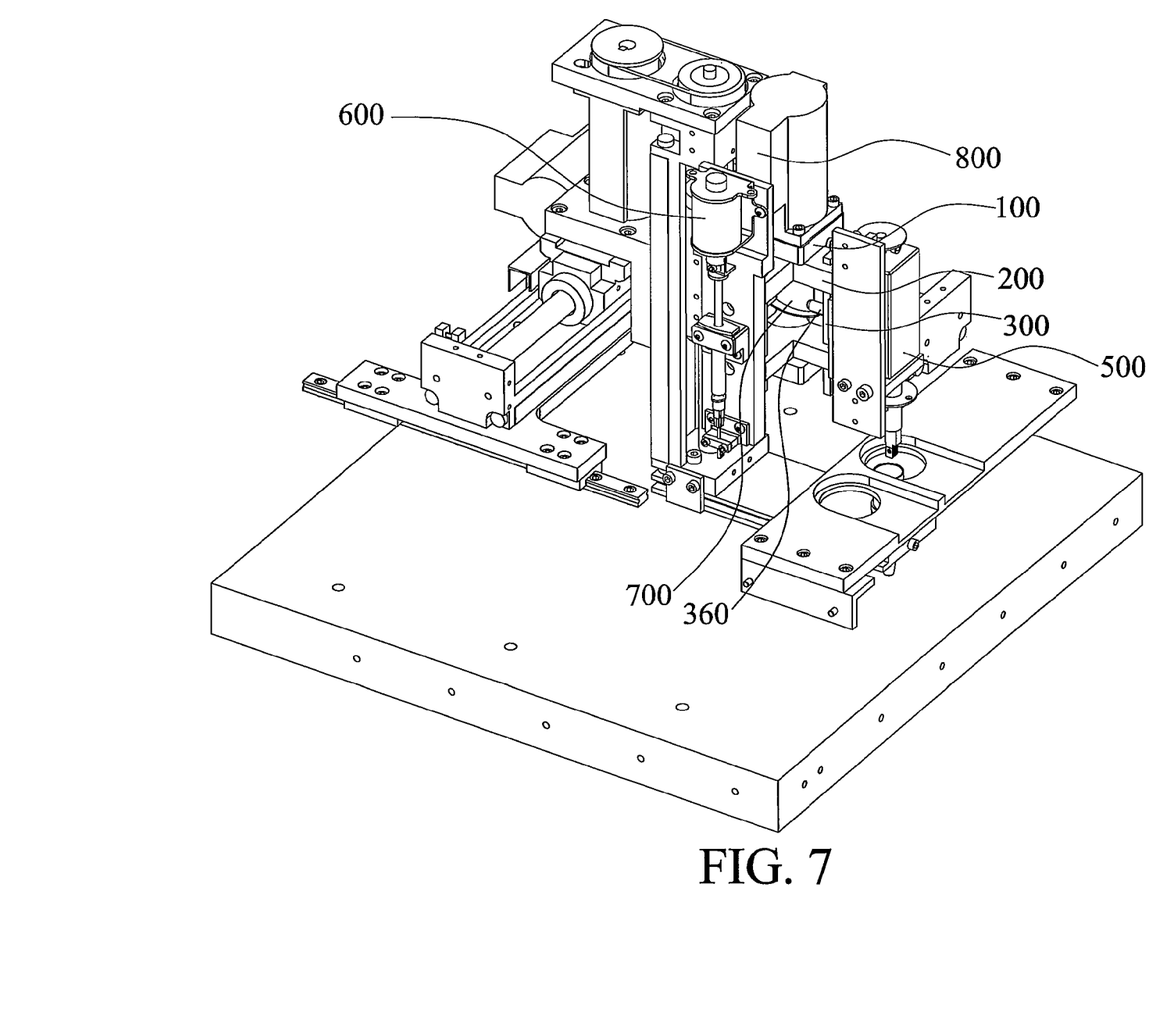
FIG. 7 depicts the aspirating device as it is lifted from the operating position to the second idle position.

Referring to FIG. 7, motor 800 rotates the holder 200 counter-clockwise to move the aspirating device 600 from the operating position to the second idle position. When the aspirating device 600 moves from the operating position to the second idle position, the second guiding element 460 moves from the lowest point 721 to the highest point 723 to lift the second sliding element 400, enabling the aspirating device 600 to rise and move to the second idle position simultaneously. FIG. 7 depicts the aspirating device 600 returning to the second idle position. The reason for lifting the aspirating device 600 is to avoid impact with other devices during the movement, which may cause damage. Because the first arm 240 holding the dissecting device 500 and the second arm 260 holding the aspirating device 600 are connected to the shaft 220, when the motor 800 rotate the holder 200 to move the aspirating device 600 from the operating position to the second idle position, the dissecting device 500 is moved from the first idle position down to the operating position by the first guiding element 360 moving from the highest point 722 to the lowest point 721.

Figure 8:
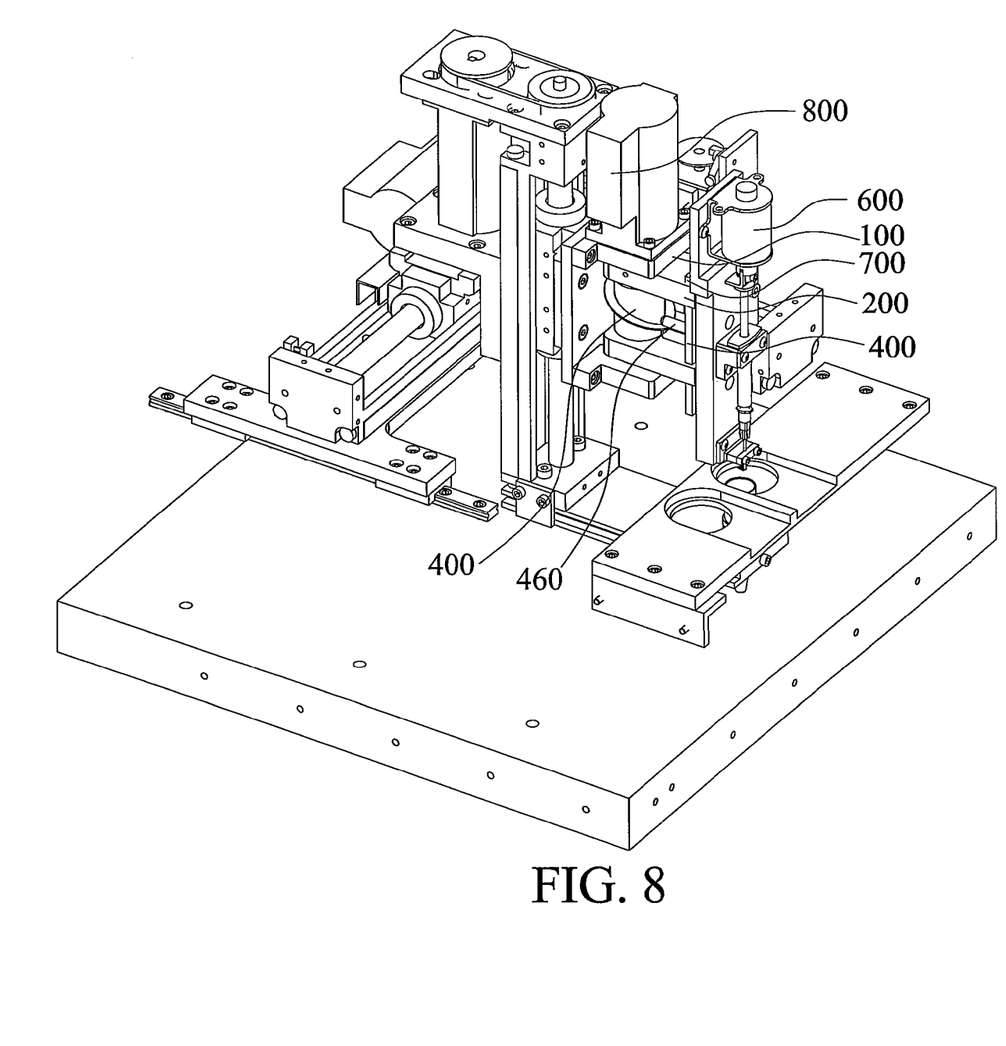
FIG. 8 depicts the aspirating device as it is lowered from the second idle position to the operating position.

FIG. 8 depicts the aspirating device 600 moved from the second idle position down to the operating position. When the aspirating device 600 is moved from the second idle position to the operating position, the dissecting device 500 is moved from the operating position up to the first idle position.

Figure 9:
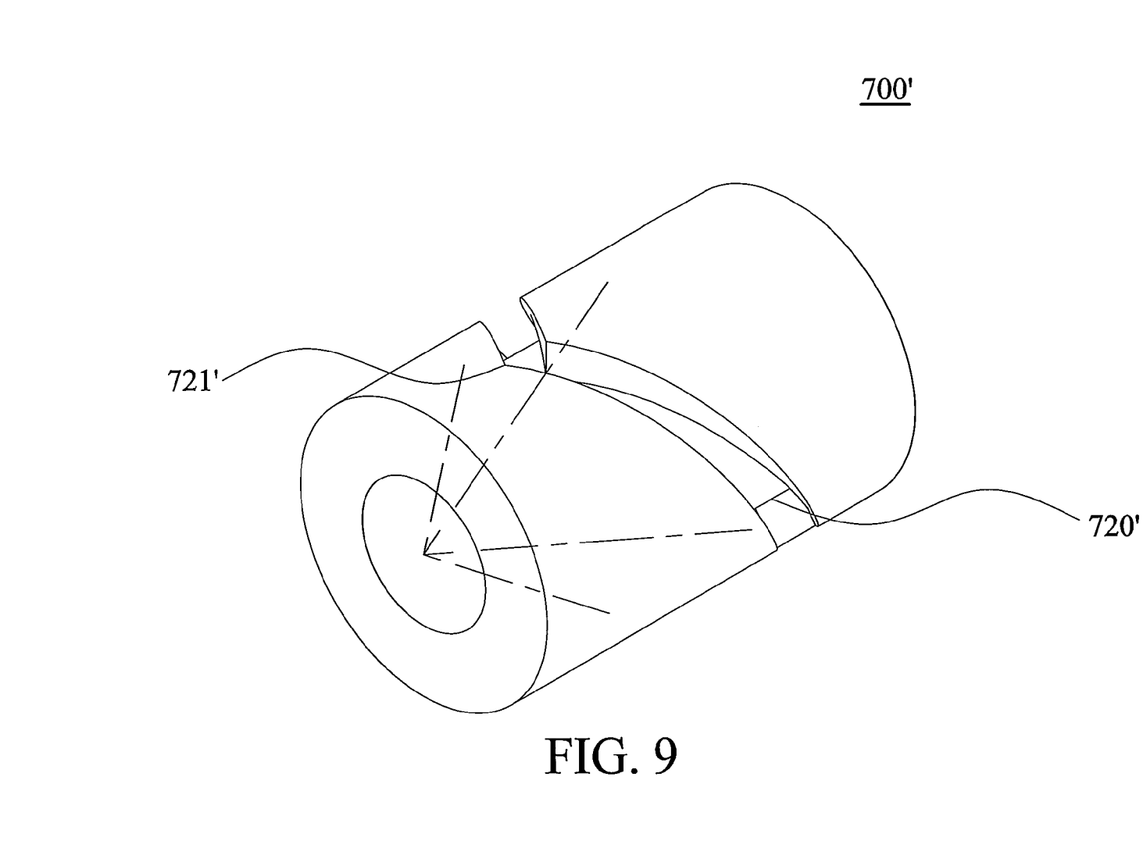
FIG. 9 is a perspective view of another embodiment of the cam of the invention.

FIG. 9 depicts another embodiment of the cam 700. In the previous embodiment, the cam 700 has a protruding track 720'. In this embodiment, the track 720' is groove-shaped. The first guiding element 360 and the second guiding element 460 abut the lateral surface of the groove-shaped track 720' for guiding. The track 720' has a lowest point 721'.

Figure 10:
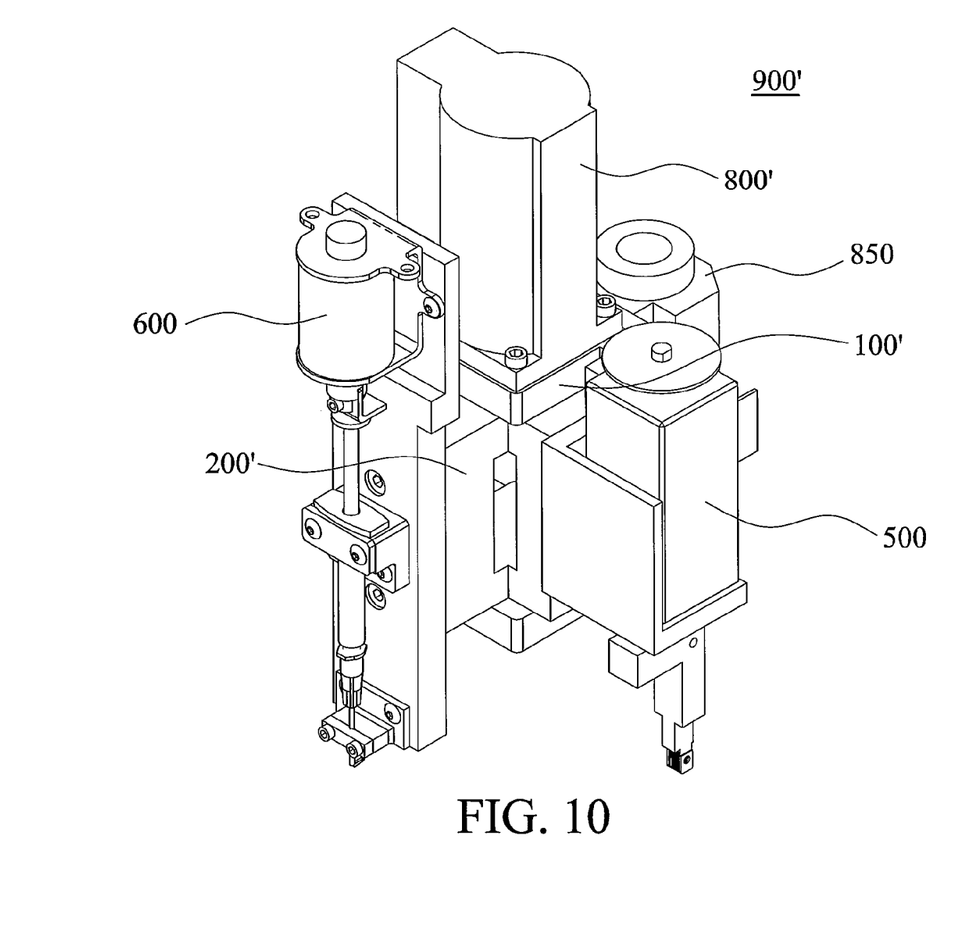
FIG. 10 is a perspective view of another embodiment of the tool exchanging mechanism of the invention.
Figure 11:
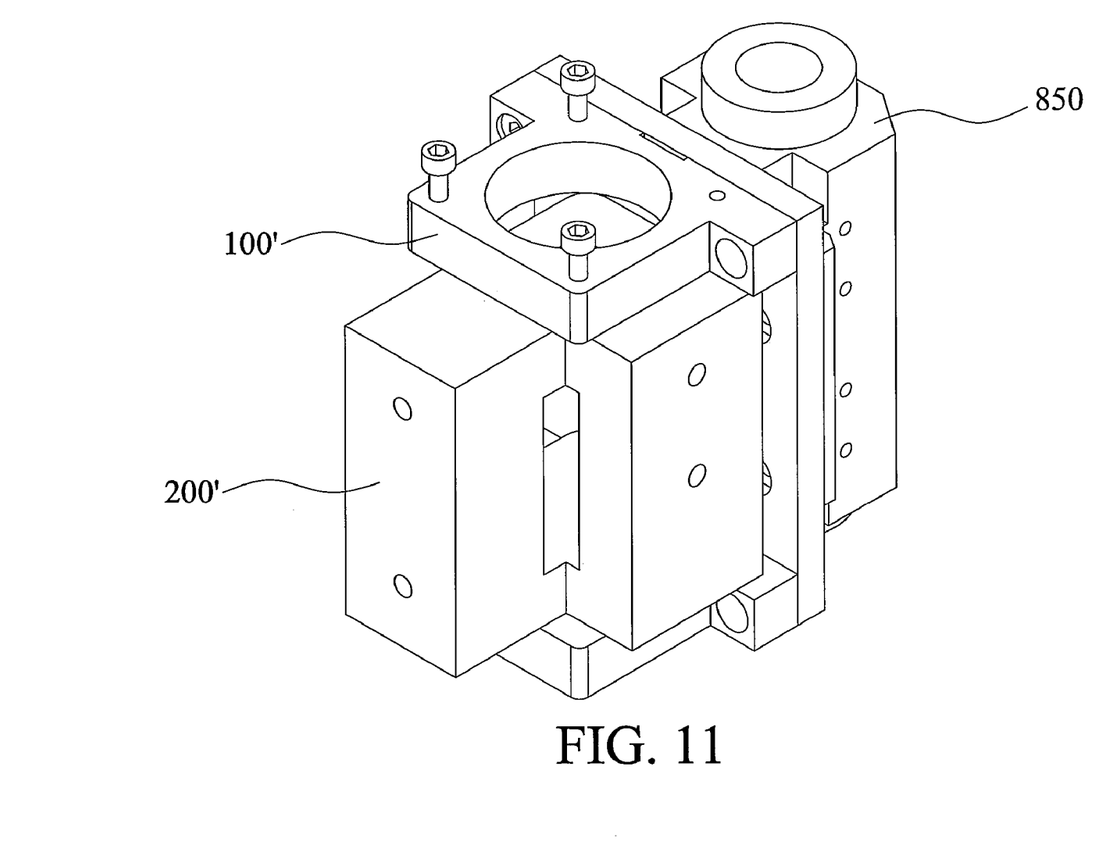
FIG. 11 depicts the holder disposed on the supporting mechanism of FIG. 10.
Figure 12:
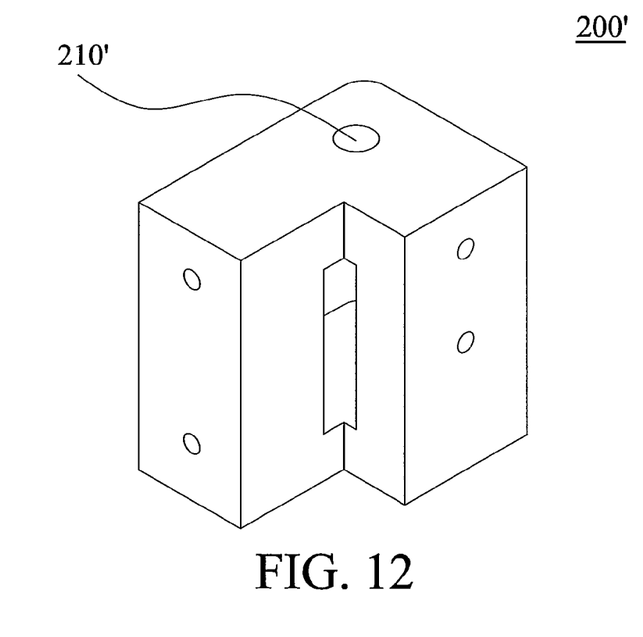
FIG. 12 is a perspective view of another embodiment of the holder.

FIG. 10 is a perspective view of another embodiment of the tool exchanging mechanism. The tool exchanging mechanism 900' comprises a supporting mechanism 100', a holder 200', a motor (first driving device) 800' and a lifting motor (second driving device) 850. The motor 800' is installed on the supporting mechanism 100' and connected to the holder 200' for rotating the holder 200'. The dissecting device 500 and the aspirating device 600 are joined to the holder 200'. FIG. 11 depicts the holder 200' installed on the supporting mechanism 100'. FIG. 12 depicts the holder 200'. The holder 200' is L-shaped and has a hole 210' engaging the axis of the motor 800', thus, the motor 800' rotates the supporting mechanism 200'. The dissecting device 500 and the aspirating device 600 are disposed on two arms of the supporting mechanism 200'. When the motor 800' rotates the holder 200', the dissecting device 500 or aspirating device 600 is moved to the operating position and the other one returns to the idle position.

To prevent the impact of the dissecting device 500 or aspirating device 600 with other devices during movement, a lifting motor 850 is disposed on the dissecting apparatus 1000. Prior to the rotation of the holder 200', the lifting motor 850 lifts the supporting mechanism 100' to an appropriate position, and the motor 800' rotates the holder 200'. The lifting motor 850 lowers the supporting mechanism 100' to move the dissecting device 500 or the aspirating device 600 into the operating position or the idle position until the dissecting device 500 or the aspirating device 600 is properly positioned.

The dissecting device and the aspirating device are installed in a tool exchanging mechanism capable of rotating, thus, the dissecting device and the aspirating device can be rapidly exchanged without impacting other devices in the dissection apparatus.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dissection apparatus, comprising
a supporting mechanism;
a holder rotatably disposed on the supporting mechanism;
a driving element disposed on the supporting mechanism to rotate the holder;
a cam fixed to the supporting mechanism, the holder rotating relative to the cam;
a first sliding element slidably disposed on the holder and lifted or lowered thereon by the guide of the cam;
a second sliding element slidably disposed on the holder and lifted or lowered thereon by the guide of the cam;
a dissecting device disposed on the first sliding element; and
an aspirating device disposed on the second sliding element, wherein when the holder rotates to move the dissecting device from a first idle position to an operating position, the first sliding element is lowered by the guide of the cam and the aspirating device is moved from the operating position to a second idle position with the second sliding element lifted by the guide of the cam, and when the holder rotates to move the aspirating device from the second idle position to the operating position, the second sliding element is lowered by the guide of the cam and the dissecting device is moved from the operating position to the first idle position with the first sliding element lifted by the guide of the cam.

2. The dissection apparatus as claimed in claim 1, wherein the cam comprises a track having a lowest point corresponding to the operating position and two highest points corresponding to the first idle position and the second idle position.

3. The dissection apparatus as claimed in claim 2, wherein the first sliding element has a first guiding element abutting the track, whereby the first sliding element slides on the holder by the guide of the cam.

4. The dissection apparatus as claimed in claim 2, wherein the second sliding element has a second guiding element abutting the track, whereby the second sliding element slides on the holder by the guide of the cam.

5. The dissection apparatus as claimed in claim 1, wherein the holder comprises a shaft, a first arm extending from the shaft and a second arm extending from the shaft, and the first sliding element is slidably disposed on the first arm and the second sliding element is slidably disposed on the second arm.

6. The dissection apparatus as claimed in claim 5, wherein the first arm is perpendicular to the second arm.

7. The dissection apparatus as claimed in claim 5, wherein the first arm has a first channel and the first sliding element has a first flange sliding in the first channel.

8. The dissection apparatus as claimed in claim 5, wherein the second arm has a second channel and the second sliding element has a second flange sliding in the second channel.

9. The dissection apparatus as claimed in claim 5, wherein the shaft is connected to the driving element, whereby the driving element rotates the shaft rotating the holder.

10. The dissection apparatus as claimed in claim 5, wherein the cam further comprises a cylindrical body and a track disposed on the periphery of the cylindrical body to guide the first sliding element and the second sliding element, the cylindrical body has a hole through which the shaft extends, whereby the holder is rotatable relative to the cam.

11. The dissection apparatus as claimed in claim 10, wherein the track is flange-shaped.

12. The dissection apparatus as claimed in claim 10, wherein the track is groove-shaped.

13. The dissection apparatus as claimed in claim 1, wherein the driving motor is a motor.

14. A dissection apparatus, comprising:
   a supporting mechanism;
   a holder rotatably disposed on the supporting mechanism;
   a first driving element disposed on the supporting mechanism to rotate the holder;
   a second driving element moving the supporting mechanism up and down;
   a dissecting device disposed on the holder; and
   an aspirating device disposed on the holder, wherein when the dissecting device is moved from a first idle position to an operating position, the second driving element moves the supporting mechanism to lift the dissecting device from the first idle position, the first driving device rotates the supporting mechanism to move the dissecting device to be above the operating position, and the second driving element lowers the supporting mechanism to move the dissecting device to the operating position and the aspirating device to a second idle position; when the aspirating device is moved from the second idle position to the operating position, the second driving element lifts the supporting mechanism to lift the aspirating device from the second idle position and the dissecting device from the operating position, the first driving element rotates the supporting mechanism to move the dissecting device to be above the operating position, and the second driving element lowers the supporting mechanism to move the aspirating device to the operating position and the dissecting device to the first idle position.

15. The dissection apparatus as claimed in claim 14, wherein the holder comprises a shaft, a first arm extending from the shaft and a second arm extending from the shaft, and the first sliding element is slidably disposed on the first arm and the second sliding element is slidably disposed on the second arm.

* * * * *